(12) United States Patent
Nagamura et al.

(10) Patent No.: US 6,600,080 B1
(45) Date of Patent: Jul. 29, 2003

(54) PRODUCING METHOD OF ALCOHOLS SUCH AS CYCLOHEXANEDIMETHANOL

(75) Inventors: Yusei Nagamura, Nishinomiya (JP); Yuuichi Satoh, Suita (JP); Jun Tatsumi, Ikoma (JP); Kunihiro Yamamura, Muko (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/676,937

(22) Filed: Oct. 2, 2000

(30) Foreign Application Priority Data

Oct. 6, 1999 (JP) ............................. 11-285611

(51) Int. Cl.⁷ .................... C07C 31/13; C07C 27/00; C07C 27/04; C07C 29/00; C07C 29/14; C07C 69/76

(52) U.S. Cl. ............................. 568/831; 568/814; 560/8

(58) Field of Search ................. 568/831, 822, 568/833, 811–814, 828, 832; 560/8, 100–107, 129

(56) References Cited

U.S. PATENT DOCUMENTS

| 3,334,149 A | 8/1967 | Akin et al. |
| 4,499,298 A | 2/1985 | Scheben et al. |
| 6,018,048 A | * 1/2000 | Morikawa et al. ......... 546/185 |

FOREIGN PATENT DOCUMENTS

| EP | 0 965 383 A1 | 12/1999 |
| JP | 52-242 | 1/1977 |
| JP | 63-174950 A | 7/1983 |
| JP | 62-273927 A | 11/1987 |
| JP | 63014745 A | * 1/1988 |
| JP | 63174950 A | * 7/1988 |
| JP | 8-187432 A | 7/1996 |
| JP | 8-231466 A | 9/1996 |
| JP | 8231466 A | * 9/1996 |
| JP | 10-7608 A | 1/1998 |
| JP | 2000-70718 A | 3/2000 |

OTHER PUBLICATIONS

Akhrem et al., Izv, Akad. Nauk SSSR, Ser. Khim., 12, pp. 2156–2161, 1996. (abstract only).*

Bull. Chem. Soc. Jpn. 1964 (vol. 37, No. 6 Jun. 1964, pp. 887–889).

Matsukata et al, Shokubai, 38(6), 1996, pp. 498–501.

Takagi et al, "Hydrogenation and Hydrogenolysis. VIII. The Ruthenium–catalyzd Hydrogenation of Aromatic Compounds Containing C–O Linkage to be Easily Hydrogenolyzed", vol. 37, No. 4, Apr. 1964, pp. 585–587.

* cited by examiner

*Primary Examiner*—Johann Righter
*Assistant Examiner*—Elvis O. Price
(74) *Attorney, Agent, or Firm*—Nixon & Vanderhye P.C.

(57) ABSTRACT

In a producing method of alcohols such as cyclohexanedimethanol, a benzyl ester is obtained, for example, by the reaction between a benzyl compound and carboxylic acid in the presence of oxygen and a catalyst including palladium, gold ultra fine particles, and at least one kind of element selected from the group consisting of Group IIA, IIIA, VIA, IIB, VB, and VIII of the periodic table, and alkali metal. The alcohols are produced by hydrogenating a benzene ring of the benzyl ester and then hydrolyzing the resultant esters. Alternatively, the benzyl ester is hydrolyzed to produce benzyl alcohols, and a benzene ring of the benzyl alcohols is hydrogenated to produce the alcohols.

13 Claims, No Drawings

PRODUCING METHOD OF ALCOHOLS SUCH AS CYCLOHEXANEDIMETHANOL

FIELD OF THE INVENTION

The present invention relates to a producing method of alcohols such as cyclohexanedimethanol. More specifically, the invention relates to a producing method of cyclohexanedimethanol via xylylene diacetate, using, for example, xylene as a starting material, and of other alcohols. Cyclohexanedimethanol is an industrially very useful compound as a raw material of polyester paint or synthetic fibers, synthetic resins, and the like.

BACKGROUND OF THE INVENTION

Conventionally known producing methods of cyclohexanedimethanol, which is an industrially very useful compound as a raw material of polyester paint or synthetic fibers, synthetic resins, and the like include: ① a method in which a benzene ring of terephthalic dialkylester used as a starting material is hydrogenated, and then the product cyclohexane dialkylester is subjected to hydrogenolysis; ② a method in which a benzene ring of terephthalic acid is hydrogenated, and then the product cyclohexane dicarboxylic acid is further hydrogenated; and ③ a method in which a benzene ring of xylylene glycol is hydrogenated to produce cyclohexanedimethanol.

Of those three producing methods, the method ① is most common and there has been many reports thereon. For example, U.S. Pat. No. 3,334,149 (published date: Aug. 1, 1967) discloses a method in which a benzene ring of terephthalic dialkylester is hydrogenated using palladium/alumina supporting catalysts, and then the ester site of the product cyclohexane dialkylester is subjected to hydrogenolysis using a copper chromite catalyst to obtain the target product cyclohexanedimethanol.

Further, for example, Japanese Unexamined Patent Publication No. 242/1977 (Tokukaisho 52-242; published date: Jan. 5, 1977), which represents the method ②, discloses a method which uses a large amount of alcohol as a solvent, wherein a benzene ring of terephthalic acid is hydrogenated using a 5% rhodium-carbon catalyst, and the product cyclohexane dicarboxylic acid is further hydrogenated using a copper chromite catalyst so as to obtain the target product cyclohexanedimethanol.

With these producing methods, the target product can be obtained with high yield. However, the methods ① and ② require exceedingly high temperature and high pressure as the reaction conditions of the hydrogenation of the benzene ring and the carbonyl group, and they require special reaction equipment. Further, stoichiometrically, these methods require 7 moles of hydrogen for 1 mole of the raw material and thus they employ a reaction which consumes a large amount of hydrogen. Further, 2 moles of alcohols and 2 moles of water are generated as a by-product respectively in the methods ① and ②, which makes the raw material unit per Kg-product larger, i.e., the cost of producing cyclohexanedimethanol is increased. Further, the copper chromite catalyst used in a later stage contains toxic chrome and there is a disposal problem. Thus, the methods ① and ② have a drawback in environmental safety. Namely, the methods ① and ② have a problem that cyclohexanedimethanol cannot be produced safely and industrially at low cost.

Meanwhile, for example, Japanese Unexamined Patent Publication No. 187432/1996 (Tokukaihei 8-187432) (published date: Jul. 23, 1996) discloses in Example 7 a method in which a benzene ring of xylylene glycol is hydrogenated under mild conditions using a Raney ruthenium catalyst as a novel hydrogenation catalyst, so as to obtain the target product cyclohexanedimethanol, i.e., method ③.

With this producing method, the target product can be obtained only by the hydrogenation of the benzene ring, and, stoichiometrically, it only requires 3 moles of hydrogen for 1 mole of the raw material, and compared with the methods ① and ②, the amount of hydrogen consumed can be reduced to less than half. Further, since alcohol and water are not generated as a by-product, the raw material unit per Kg-product can be reduced. Furthermore, since the method does not use a catalyst which contains a toxic substance, there is no disposal problem.

As to a producing method of alcohols other than the cyclohexanedimethanol, for example, Japanese Unexamined Patent Publication No. 7608/1998 (Tokukaihei 10-7608) (published date: Jan. 13, 1998) discloses a method in which benzyl alcohol is produced from benzyl acetate. Further, Document Bull. Chem. Soc. Jpn., 37, 585 (1964) in pages 585 to 587 discloses a producing method of cyclohexyl methanol from benzyl alcohol.

However, there has been no established method of inexpensively and industrially producing xylylene glycol which is used as the raw material in the method ③.

For example, Japanese Unexamined Patent Publication No. 273927/1987 (Tokukaisho 62-273927) (published date: Nov. 28, 1987) discloses a method in which p-xylene and acetic acid are allowed to react in the presence of oxygen using a catalyst containing palladium and bismuth to obtain p-xylylene diacetate, which is then used to produce p-xylylene glycol. Further, for example, Japanese Unexamined Patent Publication No. 174950/1988 (Tokukaisho 63-174950; Published date: Jul. 19, 1988) discloses a method in which p-xylene and acetic acid are allowed to react in the presence of oxygen using, as a catalyst, palladium-bismuth compound and/or palladium-lead compound to produce p-methylbenzyl acetate and p-xylylene diacetate. Further, for example, Japanese Unexamined Patent Publication No. 231466/1996 (Tokukaihei 8-231466; published date: Sep. 10, 1996) discloses a method in which p-xylene and acetic acid are allowed to react in the presence of oxygen using a palladium and gold supporting catalyst to produce p-xylylene diacetate.

However, the catalysts disclosed in Japanese Unexamined Patent Publication No. 273927/1987 and No. 174950/1988 have low catalytic activity (turnover frequency of around 15 per unit time per unit palladium in the catalyst), and thus to improve production efficiency, it requires a large amount of catalyst with respect to p-xylene as a reaction substrate, i.e., it requires a large amount of palladium as a noble metal. Further, palladium may dissolve into a reaction solution during reaction, and in this case, the catalytic activity is further reduced and it is required to separate and recover the palladium dissolved. Thus, the catalysts of the above publications may not be a catalyst suitable for a producing method in industrial applications. Further, the catalyst disclosed in Japanese Unexamined Patent Publication No. 231466/1996 also has a low catalytic activity and to improve production efficiency a large amount of catalyst is required with respect to p-xylene as a reaction substrate, and thus, as with the above example, this catalyst may not be a catalyst suitable for a producing method in industrial applications. That is, the above catalysts all have a low catalytic activity and are not suitable for a producing method in industrial applications, and thus have a problem that xylylene glycol cannot be produced efficiently and inexpensively from xylylene diacetate.

Further, Japanese Unexamined Patent Publication No. 187432/1996 does not disclose a producing method of xylylene glycol. Namely, the method ③ may not be suitable for industrially and inexpensively producing cyclohexanedimethanol since it is difficult to industrially obtain the raw material xylylene glycol.

Further, in the method of producing xylylene glycol by hydrolyzing xylylene diacetate, the reaction is known to be carried out in the presence of an alkali or acid catalyst. However, to carry out hydrolysis in the presence of an alkali, it would require twice or more moles of alkali with respect to the xylylene diacetate, and not only it is impossible to recover the acetic acid which is generated as a by-product with the xylylene glycol but a large amount of waste water is generated. Thus, the method of carrying out hydrolysis in the presence of an alkali is not suitable for a producing method in industrial applications.

On the other hand, in the case of hydrolysis in the presence of an acid catalyst such as cation exchange resin and p-toluene sulfonic acid, since the reaction takes an equilibrium and the conversion of xylylenediacetate does not become 100 percent, it is required to have a step of separating the raw material xylylene diacetate and the intermediate acetoxymethylbenzyl alcohol from the product xylylene glycol. Further, even after the usual separation and purification steps, the product xylylene glycol still contains an acetyl group containing compound as an impurity, such as a trace amount of acetic acid, xylylene diacetate, and acetoxymethylbenzyl alcohol. Note that, to completely eliminate the content (residue amount) of the acetyl group containing compound in the xylylene glycol, it requires special distillation equipment, and from the view point of economy, the method is not suitable for a producing method in industrial applications.

For example, as disclosed in Japanese Unexamined Patent Publication No. 187432/1996, in the method of producing cyclohexanedimethanol by the hydrogenation of a benzene ring of xylylene glycol, the xylylene glycol used as a raw material must not have impurities. In the case where xylylene glycol with impurities is used as a raw material, the yield of cyclohexanedimethanol is reduced significantly by the presence of the impurities therein. Particularly, because the yield of cyclohexanedimethanol depends on the content of the impurity acetyl group containing compound, the xylylene glycol containing a trace amount of acetyl group containing compound, obtained by hydrolysis, cannot be directly used in the hydrogenation as a raw material.

Namely, the conventional methods ① to ③ all have the problem that cyclohexanedimethanol cannot be produced industrially at low cost.

Further, a less expensive and industrially suitable method is also demanded for producing alcohols such as benzyl alcohol, other than the cyclohexanedimethanol.

SUMMARY OF THE INVENTION

It is an object of the present invention to provide a method of inexpensively and industrially producing alcohols such as cyclohexanedimethanol.

After extensive research by the inventors of the present application to find a producing method of cyclohexanedimethanol, it was found that the cyclohexanedimethanol can be produced both inexpensively and industrially via di(acetoxymethyl)cyclohexane from xylylene diacetate, or via xylylene glycol from xylylene diacetate, using, for example, xylene as a starting material, which can be obtained inexpensively, and found that a catalyst having a certain composition exhibits a high catalytic activity for a reaction which gives xylylene diacetate from xylene and acetic acid in the presence of oxygen, thus completing the present invention.

Further, the inventors of the present invention also conducted extensive research on a producing method of alcohols such as benzyl alcohols other than cyclohexanedimethanol, and found a method of inexpensively and industrially producing such alcohols, thus completing the present invention.

Namely, in order to achieve the foregoing object, in a producing method of cyclohexanedimethanol in accordance with the present invention, a benzene ring of xylylene diacetate is hydrogenated and thereafter a resultant di(acetoxymethyl)cyclohexane is hydrolyzed.

Also, in order to achieve the foregoing object, in the producing method of cyclohexanedimethanol in accordance with the present invention, xylylene diacetate is hydrolyzed and thereafter a benzene ring of a resultant xylylene glycol is hydrogenated.

Further, in order to achieve the foregoing object, in the producing method of cyclohexanedimethanol in accordance with the present invention, the benzene ring of the xylylene glycol is hydrogenated after adjusting the content of acetyl group containing compound in the xylylene glycol to 10 weight % or less.

Also, in order to achieve the foregoing object, in the producing method of cyclohexanedimethanol in accordance with the present invention, the xylylene diacetate is obtained by allowing xylene to react with acetic acid in the presence of oxygen.

Further, in order to achieve the foregoing object, in the producing method of cyclohexanedimethanol in accordance with the present invention, the reaction between xylene and acetic acid is carried out using a catalyst including palladium, gold ultra fine particles, and at least one kind of element selected from the group consisting of Group IIA, IIIA, VIA, IIB, VB, and VIII of the periodic table, and alkali metal.

With the foregoing method, using, for example, xylene as a starting material, which is inexpensive and can easily be obtained in industry, the xylene is reacted with acetic acid in the presence of oxygen to obtain xylylene diacetate, and cyclohexanedimethanol can be produced from the xylylene diacetate thus obtained. Also, the acetic acid which is generated as a by-product in the reaction of the xylylene diacetate to obtain cyclohexanedimethanol can be reused in the reaction with xylene. Further, the catalyst used in the reaction between xylene and acetic acid does not contain toxic substance and thus it does not cause a disposal problem, thus ensuring environmental safety.

Accordingly, it is possible to inexpensively and industrially produce cyclohexanedimethanol, which is an industrially very useful compound as a raw material of polyester paint or synthetic fibers, synthetic resins, and the like.

Further, in order to achieve the foregoing object, a producing method of alcohols in accordance with the present invention is for producing alcohols having General Formula [1],

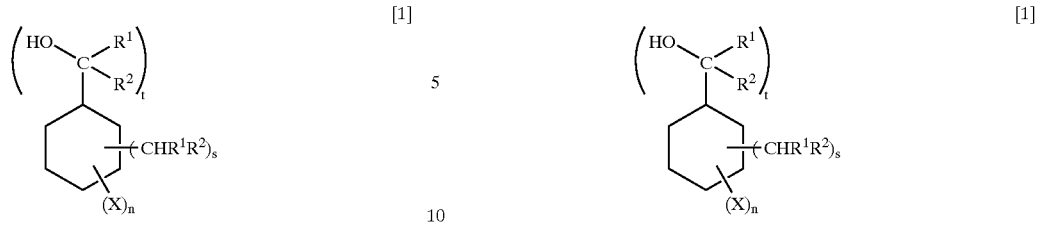

wherein:

a benzene ring of benzyl esters having General Formula [2] is hydrogenated

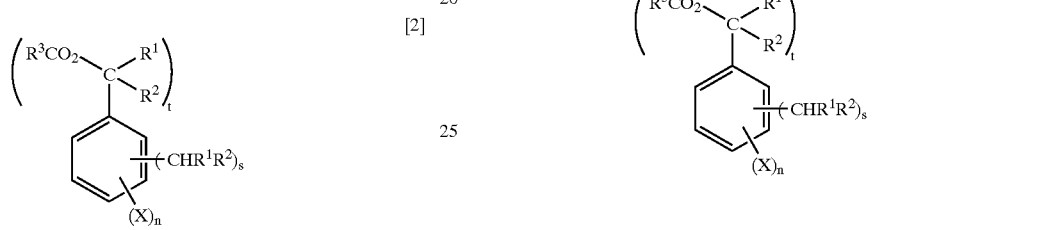

and thereafter resultant esters having General Formula [3] is hydrolyzed

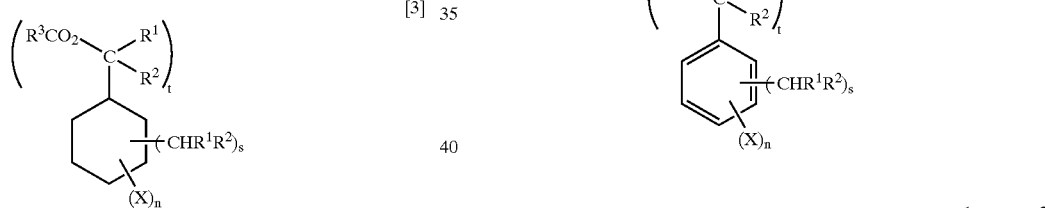

where, in General Formulae [1], [2], and [3], $R^1$ and $R^2$ are independently a hydrogen atom or alkyl group, $R^3$ is a group with a benzene ring, or an alkyl, alkenyl, or alkynyl group having 1 to 6 carbon atoms, X is a hydrogen atom, alkyl group, aryl group, hydroxy group, halogen group, nitro group, amino group, amido group, alkyloxy group, aryloxy group, carboxyl group including an alkylcarboxyl group and an arylcarboxyl group, alkyl carbonyl group, arylcarbonyl group, or carboxyalkyl group including an alkylcarboxyalkyl group and arylcarboxyalkyl group, t is an integer of 1 to 6 which indicates the number of $(CR^1R^2OH)$ group or $(CR^1R^2CO_2R^3)$ group, s is an integer of 0 to 5 which indicates the number of $(CHR^1R^2)$ group, and n is an integer of 0 to 5 which indicates the number of X, where t+s+n=6.

Further, in order to achieve the foregoing object, the producing method of alcohols in accordance with the present invention is for producing alcohols having General Formula [1], wherein:

benzyl esters having General Formula [2] are hydrolyzed

[2]

and thereafter a benzene ring of resultant benzyl alcohols having General Formula [4] is hydrogenated

[4]

where, in General Formulae [1], [2], and [4], $R^1$ and $R^2$ are independently a hydrogen atom or alkyl group, $R^3$ is a group with a benzene ring, or an alkyl, alkenyl, or alkynyl group having 1 to 6 carbon atoms, X is a hydrogen atom, alkyl group, aryl group, hydroxy group, halogen group, nitro group, amino group, amido group, alkyloxy group, aryloxy group, carboxyl group including an alkylcarboxyl group and an arylcarboxyl group, alkyl carbonyl group, arylcarbonyl group, or carboxyalkyl group including an alkylcarboxyalkyl group and arylcarboxyalkyl group, t is an integer of 1 to 6 which indicates the number of $(CR^1R^2OH)$ group or $(CR^1R^2CO_2R^3)$ group, s is an integer of 0 to 5 which indicates the number of $(CHR^1R^2)$ group, and n is an integer of 0 to 5 which indicates the number of X, where t+s+n=6.

Further, in order to achieve the foregoing object, in the producing method of alcohols in accordance with the present invention, the benzyl esters of General Formula [2] are obtained by allowing a benzyl compound having General Formula [5] to react with a carboxylic acid of the formula $R^3COOH$ in the presence of oxygen

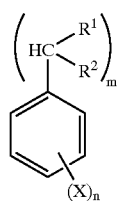

where, in General Formula [5], m is an integer of 1 to 6 which indicates the number of $(CR^1R^2H)$ group, and t+s=m.

Further, in order to achieve the foregoing object, in the producing method of alcohols in accordance with the present invention, the reaction between the benzyl compound of General Formula [5] and the carboxylic acid is carried out using a catalyst including palladium, gold ultra fine particles, and at least one kind of element selected from the group consisting of Group IIA, IIIA, VIA, IIB, VB, and VIII of the periodic table, and alkali metal.

Further, in order to achieve the foregoing object, in the producing method of alcohols in accordance with the present invention, acrylic acid or methacrylic acid is used as the carboxylic acid.

Further, in order to achieve the foregoing object, in the producing method of alcohols in accordance with the present invention, the benzene ring of the benzyl esters of General Formula [2] is hydrogenated after adjusting the content of carboxylic acid in the benzyl esters to 10 weight % or less.

Further, in order to achieve the foregoing object, in the producing method of alcohols in accordance with the present invention, the benzene ring of the benzyl alcohols of General Formula [4] is hydrogenated after adjusting the content of acetyl group containing compound in the benzyl alcohols to 10 weight % or less.

Further, in order to achieve the foregoing object, the producing method of alcohols in accordance with the present invention is for producing alcohols having General Formula [1],

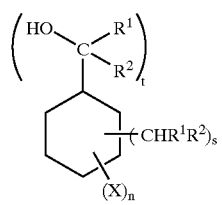

wherein:

a benzene ring of benzyl alcohols having General Formula [4] is hydrogenated after adjusting a content of acetyl group containing compound in the benzyl alcohols to 10 weight % or less

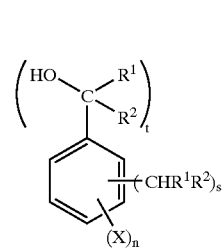

where, in General Formulae [1] and [4], $R^1$ and $R^2$ are independently a hydrogen atom or alkyl group, $R^3$ is a group with a benzene ring, or an alkyl, alkenyl, or alkynyl group having 1 to 6 carbon atoms, X is a hydrogen atom, alkyl group, aryl group, hydroxy group, halogen group, nitro group, amino group, amido group, alkyloxy group, aryloxy group, carboxyl group including an alkylcarboxyl group and an arylcarboxyl group, alkyl carbonyl group, arylcarbonyl group, or carboxyalkyl group including an alkylcarboxyalkyl group and arylcarboxyalkyl group, t is an integer of 1 to 6 which indicates the number of $(CR^1R^2OH)$ group, s is an integer of 0 to 5 which indicates the number of $(CHR^1R^2)$ group, and n is an integer of 0 to 5 which indicates the number of X, where t+s+n=6.

Further, in order to achieve the foregoing object, the producing method of alcohols in accordance with the present invention is for producing benzyl alcohols having General Formula [4],

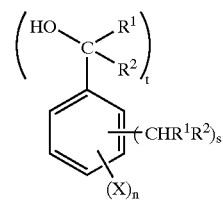

wherein:

using a catalyst including palladium, gold ultra fine particles, and at least one kind of element selected from the group consisting of Group IIA, IIIA, VIA, IIB, VB, and VIII of the periodic table, and alkali metal, a benzyl compound having General Formula [5] is allowed to react with a carboxylic acid of the formula $R^3COOH$ in the presence of oxygen,

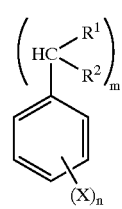

and thereafter a resultant benzyl ester having General Formula [2] is hydrolyzed,

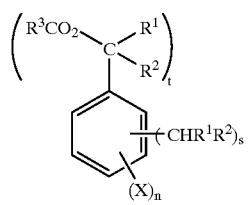

[2]

where, in General Formulae [2], [4], and [5], $R^1$ and $R^2$ are independently a hydrogen atom or alkyl group, $R^3$ is a group with a benzene ring, or an alkyl, alkenyl, or alkynyl group having 1 to 6 carbon atoms, X is a hydrogen atom, alkyl group, aryl group, hydroxy group, halogen group, nitro group, amino group, amido group, alkyloxy group, aryloxy group, carboxyl group including an alkylcarboxyl group and an arylcarboxyl group, alkyl carbonyl group, arylcarbonyl group, or carboxyalkyl group including an alkylcarboxyalkyl group and arylcarboxyalkyl group, t is an integer of 1 to 6 which indicates the number of ($CR^1R^2OH$) group or ($CR^1R^2CO_2R^3$) group, s is an integer of 0 to 5 which indicates the number of ($CHR^1R^2$) group, and n is an integer of 0 to 5 which indicates the number of X, where t+s+n=6, and m is an integer of 1 to 6 which indicates the number of ($CR^1R^2H$) group, and t+s=m.

With the foregoing method, using, for example, benzyl compounds such as xylene and toluene as a starting material, which are inexpensive and can easily be obtained in industry, a benzyl compound is reacted with a carboxylic acid such as acetic acid or (meth)acrylic acid in the presence of oxygen to obtain benzyl ester, and alcohols such as benzyl alcohol can be produced from the benzyl ester thus obtained. Also, the carboxylic acid which is generated as a by-product in the reaction of the benzyl ester to obtain alcohols such as benzyl alcohol can be reused in the reaction with the benzyl compound. Further, the catalyst used in the reaction between the benzyl compound and carboxylic acid does not contain toxic substance and thus it does not cause a disposal problem, thus ensuring environmental safety.

Accordingly, it is possible to inexpensively and industrially produce alcohols such as benzyl alcohol, which are industrially very useful compounds.

For a fuller understanding of the nature and advantages of the invention, reference should be made to the ensuing detailed description taken in conjunction with the accompanying drawings.

DESCRIPTION OF THE EMBODIMENTS

A producing method of cyclohexanedimethanol in accordance with the present invention is the method in which a benzine ring of xylylene diacetate is hydrogenated, and thereafter the product di(acetoxymethyl)cyclohexane is hydrolyzed. Further, the producing method of cyclohexanedimethanol in accordance with the present invention is the method in which xylylene diacetate is hydrolyzed, and thereafter a benzene ring of the product xylylene glycol is hydrogenated. The xylylene diacetate is obtained, for example, by the reaction between xylene and acetic acid (oxidative acetoxylation reaction) in the presence of oxygen and a catalyst including palladium, gold ultra fine particles, and at least one kind of element selected from the group consisting of Group IIA, IIIA, VIA, IIB, VB, and VIII of the periodic table, and alkali metal.

Note that, in the present invention, "ultra fine particles" refers to those particles with a particle size in the order of nano meters (nm). Also, in the present invention, it is deemed that "elements in Group VIII of the periodic table" do not include palladium.

The following describes a process for preparation of the catalyst. The catalyst in accordance with the present invention can be prepared ① by a process in which after obtaining gold ultra fine particles by the heat treatment of a gold compound at a temperature of 150° C. to 800° C., the gold ultra fine particles are mixed with a palladium compound and a compound ("third compound" hereinafter) containing at least one kind of element selected from the group consisting of Group IIA, IIIA, VIA, IIB, VB, and VIII of the periodic table, and alkali metal, or ② by a process in which after obtaining a mixture containing gold ultra fine particles and palladium by the heat treatment of a gold compound and a palladium compound at a temperature of 150° C. to 800° C., the mixture is mixed with the third compound.

Specifically, as the palladium compound used to prepare the catalyst, for example, the following compounds but not limited to these are available: metal palladium, palladium oxide, palladium nitrate, palladium sulfate, palladium acetate, ammonium hexachloro palladate, sodium hexachloro palladate, potassium hexachloro palladate, ammonium tetrachloro palladate, sodium tetrachloro palladate, potassium tetrachloro palladate, potassium tetrabromo palladate, potassium tetracyano palladate, palladium chloride, palladium bromide, palladium iodide, chlorocarbonyl palladium, potassium dinitrosulfite palladate, dinitrodiamine palladium, tetraammine palladium chloride, tetraammine palladium nitrate, cis-dichlorodiamine palladium, trans-dichlorodiamine palladium, bistriphenyl phosphine palladium dichloride, and dichloro(ethylenediamine) palladium. These palladium compounds may be used individually or in combination of two or more kinds. Of those palladium compounds as exemplified above, a water-soluble compound is preferable, and palladium nitrate, palladium sulfate, palladium acetate, palladium chloride, and tetraammine palladium chloride are more preferable, and palladium acetate and tetraammine palladium chloride are particularly preferable. Note that, the palladium compounds may be a hydrate.

As the gold compound used to prepare the catalyst, a water-soluble compound is adopted. Specifically, as the gold compound, for example, the following compounds but not limited to these are available: a complex such as tetrachloroauric (III) acid "$H[AuCl_4]$", sodium tetrachloroauric (III) acid "$Na[AuCl_4]$", potassium dicyanoaurous (I) acid "$K[Au(CN)_2]$", and diethylamineauric (III) acid trichloride "$(C_2H_5)_2NH.[AuCl_3]$", and gold cyanide (I) "AuCN". These gold compounds may be used individually or in combination of two or more kinds. Of those gold compounds as exemplified above, tetrachloroauric (III) acid is particularly preferable. Note that, the gold compounds may be a hydrate.

The third compound used to prepare the catalyst includes at least one kind of element selected from the group consisting of Group IIA, IIIA, VIA, IIB, VB, and VIII of the periodic table, and alkali metal, and more preferably it includes at least one kind of element selected from the group consisting of bismuth, molybdenum, iron, nickel, zinc, lanthanum, alkali earth metal, and alkali metal.

Specifically, as the third compound, for example, the following compounds but not limited to these are available: bismuth compounds such as bismuth acetate, bismuth acetate oxide, bismuth fluoride, bismuth chloride, bismuth bromide, bismuth iodide, bismuth oxide, bismuth hydroxide, bismuth oxychloride, bismuth nitride, and basic bismuth carbonate; molybdenum compounds such as molybdic acid, sodium molybdate, molybdenum borate, molybdenum chloride, molybdenum oxide, phosphomolybdic acid (molybdophosphoric acid), silico molybdic acid (molybdosilicic acid), molybdenum acetylacetonate oxide, and molybdenum hexacarbonyl; iron compounds such as iron nitrate, iron sulfate, iron phosphate, iron chloride, iron bromide, iron acetate, iron oxalate, and iron acetylacetonate; nickel compounds such as nickel acetate, nickel chloride, nickel bromide, nickel carbonate, nickel oxide, nickel hydroxide, nickel nitrate, nickel sulfate, nickel cyanide, and nickel acetylacetonate; zinc compounds such as zinc acetate, zinc chloride, zinc bromide, zinc iodide, zinc carbonate, zinc oxide, zinc nitrate, zinc sulfate, zinc phosphate, zinc cyanide, and zinc acetylacetonate; lanthanum acetate, lanthanum oxalate, lanthanum chloride, lanthanum bromide, lanthanum carbonate, lanthanum oxide, lanthanum nitrate, lanthanum sulfate, and lanthanum acetylacetonate; alkali metal compounds such as acetate, nitrate, sulfate, halogenated product, or oxide of an alkali metal, and alkali metal acetylacetonate; and alkali earth metal compounds such as acetate, nitrate, sulfate, halogenated product, or oxide of an alkali earth metal, and alkali earth metal acetylacetonate.

These third compounds may be used individually or in combination of two or more kinds. Of those third compounds as exemplified above, bismuth compounds, alkali metal compounds, and alkali earth metal compounds are more preferable, and bismuth acetate, bismuth acetate oxide, bismuth nitrate, potassium acetate, sodium acetate, secium acetate, potassium nitrate, barium acetate, and barium nitrate are particularly preferable. Note that, the third compounds may be a hydrate.

In the preparation method of the catalyst in accordance with the present invention, specifically, the gold ultra fine particles may be obtained by the method in which, for example, a support is immersed in an aqueous solution containing a gold compound and a surfactant, and after a gold precipitate is deposited on the support, the support is subjected to a heat treatment at a temperature of 150° C. to 800° C. so as to immobilize the gold precipitate. Further, in the preparation method of the catalyst in accordance with the present invention, the mixture of gold ultra fine particles and palladium may be obtained by the method in which, for example, a support is immersed in an aqueous solution including a gold compound, a palladium compound, and a surfactant, and after a gold precipitate and palladium precipitate is deposited on the support, the support is subjected to a heat treatment at a temperature of 150° C. to 800° C. so as to immobilize the gold precipitate and the palladium precipitate. That is, the gold ultra fine particles are preferably immobilized on a support.

As the support, a porous inorganic substance and active carbon are suitably adopted. Specifically, as the porous inorganic substance, for example, the following compounds but not limited to these are available: titanium oxide (titania), zirconium oxide (zirconia), silicon oxide (silica), aluminum oxide (alumina), silica.alumina, silica.titania, silica.zirconia, titania.zirconia, titania.alumina, zirconia.alumina, zeolite, silica gel, magnesium oxide (magnesia), silica.magnesia, clay, bauxite, diatomaceous earth, and pumice.

These supports may be used individually or in combination of two or more kinds. It is further preferable that the support includes at least one kind of substance selected from the group consisting of titanium oxide, zirconium oxide, and aluminum oxide. Here, for example, by "including titanium oxide", it is meant that the support includes titanium oxide, or titanium oxide is immobilized on a surface of the support (on the support) made of an inorganic substance other than titanium oxide. The crystalline structure of the titanium oxide is not particularly limited but it is preferably amorphous or anatase type. Note that, the inorganic substances, for example, such as titanium oxide, zirconium oxide, silicon oxide, and aluminum oxide may be a hydrate.

Further, in the case where titanium oxide is immobilized on the surface of the support, it is particularly preferable that the titanium oxide is immobilized while being dispersed on the support surface in a so-called "island arrangement". Note that, the titanium oxide may alternatively be immobilized on the surface of the support by a process such as coating. Further, other inorganic substances other than titanium oxide may be immobilized on the support.

The specific surface area of the support is not particularly limited but it is preferably not less than 50 $m^2/g$. When the specific surface area is less than 50 $m^2/g$, the amount of immobilized gold ultra fine particles may be reduced. That is, the catalytic activity may be reduced. Further, in the case where the support is a molding support, the shape or size of the molding support, and the molding method are not particularly limited.

The amount of gold compound used depends on the type, specific surface area, shape, and the amount of the support used, but is preferably the amount which would make the concentration of the gold compound in the aqueous solution to fall in a range of 0.01 mmole/L to 10 mmole/L. The concentration below 0.01 mmole/L reduces the amount of gold precipitate deposited and is not preferable. The concentration which exceeds 10 mmole/L facilitates aggregation of gold and increases the particle size of the gold precipitate, i.e., the particle size of gold particles immobilized, which fails to generate ultra fine particles and is not preferable. When the catalyst does not include the gold ultra fine particles, the catalytic activity is significantly reduced.

As the surfactant, for example, the following compounds but not limited to these are available: anionic surfactants such as long chain alkyl sulfonic acid and its salt, long chain alkylbenzene sulfonic acid and its salt, long chain alkyl carboxylic acid and its salt; cationic surfactants such as long chain alkyl quaternary ammonium salt; and nonionic surfactants such as polyalkylene glycol and polyoxyethylene nonylphenol. These surfactants may be used individually or in combination of two or more kinds. Of these surfactants as exemplified above, anionic surfactants and nonionic surfactants are preferable and anionic surfactant is particularly preferable. Further, among the anionic surfactants, long chain alkyl(aryl)sulfonic acid having 8 or more carbon atoms and its salt, and long chain alkyl(aryl)carboxylic acid and its salt are more preferable.

The amount is surfactant used is set in accordance with types and combinations of surfactant, gold compound, palladium compound, and support, and is not particularly limited, but it is preferably the amount which would make the concentration of the surfactant in the aqueous solution to fall in a range of 0.1 mmole/L to 10 mmole/L. At the concentration below 0.1 mmole/L, the effect of the surfactant may not be obtained. At the concentration exceeding 10 mmole/L, essentially no further effect can be expected as compared with the concentration in the above range. Further, the concentration exceeding 10 mmole/L complicates the washing process for washing the support on which the gold precipitate (and palladium precipitate) have been deposited.

The aqueous solution can easily be prepared by dissolving the gold compound, the palladium compound (as required), and the surfactant in water, and by adjusting the pH. The pH of the aqueous solution is adjusted to be preferably in a range of 6 to 10. By adjusting the pH of the aqueous solution in this range, gold precipitates in the form of ultra fine particles are generated. Note that, the preparation method of the aqueous solution is not particularly limited.

To adjust the pH of the aqueous solution in the above range, an alkaline compound is appropriately added. Specifically, as such a compound, for example, sodium carbonate, potassium carbonate, sodium hydroxide, potassium hydroxide, ammonia, and the like are available but not limited to these. The compound may be added in a solid state or by being dissolved in water.

The support is added while stirring the aqueous solution to immerse the support therein. The support thus immersed, by being stirred, is dispersed and suspended in the aqueous solution, and the gold precipitate (and palladium precipitate) are deposited on the support surface. Specifically, the gold precipitate may be, for example, gold hydroxide or gold ultra fine particles. The gold precipitate has a relatively narrow distribution of particle size. Note that, the supporting method is not particularly limited and various methods such as precipitation method, ion exchange method, impregnation method, and deposition method can be adopted.

The deposition temperature at which the gold precipitate is deposited on the support is preferably in a range of 30° C. to 80° C. Further, the deposition time of 10 minutes to 3 hours is sufficient. Note that, the amount of gold precipitate deposited on the support may be increased by repeating the deposition process as required but only to the extent where the particle size of the gold precipitate deposited does not become too large.

By the above process, the gold precipitate (and palladium precipitate) are efficiently deposited on the surface of the support and a gold precipitate immobilized product is obtained. With this process, since the aqueous solution includes a surfactant, even when, for example, the support is a molding support or when the point of zero charge on the support surface is relatively small, a larger amount of gold precipitate can be deposited on the support than conventionally. Desirably, the content of gold in the gold precipitate immobilized product is to be large but a range of 0.01 weight % to 20 weight % is preferable and a range of 0.1 weight % to 5 weight % is more preferable. Note that, the gold precipitate immobilized product may be water washed as required to remove the surfactant adhering on the surface.

Then, by subjecting the gold precipitate immobilized product to a heat treatment at a temperature of 150° C. to 800° C., or more specifically by heating and calcining the gold precipitate immobilized product in air to a temperature of 150° C. to 800° C., or more preferably to 300° C. to 800° C., a product containing gold ultra fine particles, or a product of a mixture containing gold ultra fine particles and palladium ("gold ultra fine particles immobilized product" hereinafter) is obtained. Note that, when the gold precipitate is a gold hydroxide, it becomes gold ultra fine particles by being decomposed by heat.

The calcining method is not particularly limited. For example, the calcining atmosphere is not particularly limited and it may be in the air, or in an inert gas such as nitrogen gas, helium gas, and argon gas, or a reducing gas such as hydrogen gas. Further, the heating time is set in accordance with the heating temperature and it is not particularly limited. By calcining, the gold ultra fine particles are firmly immobilized on the surface of the support, thus preparing the gold ultra fine particles immobilized product. Note that, the method of obtaining the gold ultra fine particles immobilized product is not just limited to the method as exemplified above.

When the gold ultra fine particles immobilized product does not include palladium, the catalyst in accordance with the present invention is prepared by mixing the gold ultra fine particles immobilized product with the palladium compound and the third compound. When the gold ultra fine particles immobilized product includes palladium, the catalyst in accordance with the present invention is prepared by mixing the gold ultra fine particles immobilized product with the third compound. Note that even when the gold ultra fine particles immobilized product includes palladium, the palladium compound may be added as required.

The method and order of mixing the gold ultra fine particles immobilized product with the palladium compound and the third compound are not particularly limited. Further, when subjecting xylene and acetic acid. to the oxidative acetoxylation reaction, i.e., when synthesizing the xylylene diacetate, the gold ultra fine particles immobilized product, the palladium compound, and the third compound may be placed into a reaction apparatus together with the xylene and acetic acid as the raw material. That is, the catalyst in accordance with the present invention may alternatively be prepared by mixing these immobilized product and compounds in the reaction apparatus when synthesizing the xylylene diacetate.

The catalyst prepared by the foregoing method, i.e., the catalyst in accordance with the present invention includes palladium, gold ultra fine particles, and at least one kind of element ("third metal component" hereinafter) selected from the group consisting of Group IIA, IIIA, VIA, IIB, VB, and VIII of the periodic table, and alkali metal.

The ratio of palladium, gold ultra fine particles, and third metal component, i.e., the composition of the catalyst is not particularly limited, but the proportion of palladium in the catalyst is preferably in a range of 0.001 weight % to 10 weight %, and more preferably in a range of 0.1 weight % to 2 weight %. The proportion of gold ultra fine particles in the catalyst is preferably in a range of 0.001 weight % to 10 weight %, and more preferably in a range of 0.1 weight % to 5 weight %. The proportion of third metal component in the catalyst is preferably in a range of 0.0001 weight % to 10 weight %, and more preferably in a range of 0.001 weight % to 2 weight %. The amount of palladium and gold ultra fine particles below these proportion ranges reduces the catalytic activity and is not preferable. The amount of palladium and gold ultra fine particles exceeding these proportion ranges increases the production cost of the catalyst and the xylylene diacetate cannot be produced inexpensively.

Thus, the palladium compound, the gold compound, and the third compound are used with such proportions that the composition of the catalyst is in the above ranges. The catalyst obtained by the above preparation method has higher activity than the conventional catalyst and can be suitably adopted for the oxidative acetoxylation reaction (particularly in a producing method in industrial applications) between xylene and acetic acid. Further, since the catalyst does not contain toxic substance, there is no disposal problem, thus ensuring environmental safety.

The following describes a synthesis method of the xylylene diacetate. The xylene used as a starting material in the producing method of the cyclohexanedimethanol in accordance with the present invention may be any of three different isomers or a mixture of these, but p-xylene is more preferable. The mole ratio of acetic acid with respect to xylene is to be larger than the stoichiometric ratio and is not particularly limited, but a range of 1:1 to 20:1 is more preferable. When the mole ratio is below 1:1, the acetic acid will be deficient and the xylylene diacetate may not be produced efficiently. On the other hand, even when the acetic acid is used at a mole ratio which exceeds 20:1, a further improvement in yield, etc., cannot be expected as compared with the mole ratio in the above range. In fact, in such a case, since the acetic acid is used in a large amount, it might increase the size of the reaction apparatus and the recovering device for recovering the excess acetic acid, thus possibly increasing the production cost, including the recovering cost.

By the oxidative acetoxylation reaction between xylene and acetic acid in the presence of the catalyst, the xylylene diacetate [$CH_3COOCH_2$—$C_6H_4$—$CH_2OCOCH_3$] is obtained. The reaction is carried out in a liquid phase or gaseous phase in the presence of an oxygen gas (molecular oxygen). That is, in the present invention, the oxidation reaction may be carried out in a liquid phase or gaseous phase but the liquid phase is more preferable. The oxygen gas may be diluted with an inert gas such as nitrogen gas, helium gas, or argon gas. Further, air may be used as the gas including oxygen. The supply method of the oxygen gas into the reaction system is not particularly limited.

The reaction may be any of a continuous type, batch type, and semibatch type, and is not particularly limited. For example, when the reaction is of a batch type, the catalyst is fed to the reaction apparatus together with the raw material, and in the case of a continuous type, for example, the catalyst is introduced into the reaction apparatus in advance, or it is fed to the reaction apparatus continuously with the raw material. Thus, the catalyst may be used in any of a fixed bed, fluidized bed, and suspension bed.

The amount of catalyst used with respect to the xylene is not particularly limited, and it is set in accordance with the mole ratio of acetic acid with respect to xylene, the composition of the catalyst, and reaction conditions, etc. Reaction conditions such as reaction temperature, reaction pressure, and reaction time are not particularly limited, and they are set in accordance with the mole ratio of acetic acid with respect to xylene, the composition and amount of catalyst used, etc., and a reaction temperature in a range of 80° C. to 200° C. is preferable. A reaction temperature below 80° C. slows down the reaction rate and the xylylene diacetate may not be synthesized efficiently. On the other hand, a reaction temperature exceeding 200° C. facilitates a side reaction including combustion and the xylylene diacetate may not be synthesized efficiently. Further, corrosion of the reaction apparatus by the acetic acid may be induced.

The reaction pressure is not particularly limited and may be either of reduced pressure, ordinary pressure (atmospheric pressure) and applied pressure, and a pressure in a range of ordinary pressure to $9.81\times10^6$ pa (gauge pressure) is preferably applied to increase the oxygen concentration in the reaction solution. A reaction pressure exceeding $9.81\times10^6$ pa is not preferable from an industry stand point such as reaction equipment, etc. Note that, the oxidative acetoxylation reaction does not particularly require a solvent since the xylene and acetic acid are used in a liquid form, but it may be diluted as required using a solvent which is inactive toward the reaction.

By the above method, the xylylene diacetate is obtained with the intermediate methylbenzyl acetate [$CH_3$—$C_6H_4$—$CH_2OCOCH_3$] as a reaction intermediate. More specifically, when p-xylene is used as the raw material, p-xylylene diacetate is obtained with 4-methylbenzyl acetate as a by-product. To separate, recover, and purify (optional) the xylylene diacetate and methylbenzyl acetate from the reaction liquid, a common method such as distillation may be adopted but the method of separation, recovery, and purification is not particularly limited. The xylylene diacetate after separation, recovery, and purification (optional) is subjected to a reaction of a later stage. The methylbenzyl acetate after separation, recovery, and purification may be made into the xylylene diacetate by subjecting it again to the oxidative acetoxylation reaction.

The target product cyclohexanedimethanol is produced either by hydrogenating a benzene ring of the xylylene diacetate thus synthesized by the above method and then hydrolyzing the product di(acetoxymethyl)cyclohexane, or by hydrolyzing the xylylene diacetate and then hydrogenating a benzene ring of the product xylylene glycol.

The following describes a producing method of the cyclohexanedimethanol from xylylene diacetate via di(acetoxymethyl)cyclohexane.

The method of hydrogenating the benzene ring of the xylylene diacetate is not particularly limited and any conventionally known method can be adopted. More specifically, for example, hydrogenation may be carried out by a common method wherein the reaction with hydrogen is carried out using a reducing catalyst such as (i) a noble metal supporting catalyst in which a noble metal (Pt group) such as palladium, platinum, ruthenium, rhodium, or iridium is immobilized on a support such as active carbon, alumina, or diatomaceous earth, (ii) a noble metal oxide such as palladium oxide, platinum oxide, ruthenium oxide, rhodium oxide, or iridium oxide, (iii) a noble metal simple substance such as palladium black, platinum black, ruthenium black, or rhodium black; (iv) a Raney catalyst such as Raney nickel, Raney cobalt, Raney ruthenium; and (v) a base metal supporting catalyst supporting a base metal on a support.

Hydrogen is used in excess of the xylylene diacetate. Accordingly, the mole ratio of hydrogen with respect to xylylene diacetate and the supply method of hydrogen are not particularly limited. Further, the amount of reducing catalyst used with respect to the xylylene diacetate is set in accordance with the composition of the reducing catalyst, reaction conditions, and supply method of hydrogen, etc., and is not particularly limited. Reaction conditions such as reaction temperature, reaction pressure, and reaction time are set in accordance with the composition and the amount of reducing catalyst used and the supply method of hydrogen, etc., and are not particularly limited but a reaction temperature of ordinary temperature to 250° C. is preferable and 50° C. to 200° C. is most preferable. A reaction temperature below ordinary temperature (25° C.) may slow the reaction rate significantly. On the other hand, a reaction temperature exceeding 250° C. may induce side reactions. Further, the reaction pressure is preferably an applied pressure. Note that, the hydrogenation reaction may not necessarily require a solvent but may be diluted as required using a solvent which is inactive toward the reaction.

By the above reaction, di(acetoxymethyl)cyclohexane [$CH_3COOCH_2$—$C_6H_{10}$—$CH_2OCOCH_3$] is obtained. More specifically, when p-xylene is used as the starting material, 1,4-di(acetoxymethyl)cyclohexane is obtained. Note that, the di(acetoxymethyl)cyclohexane is fed to a reaction of the following stage after filtering out the reducing catalyst.

The catalyst used in the reduction reaction is easily separated and recovered from the reaction liquid by common methods such as filtration and distillation. Further, the resultant product, unreacted raw material, and solvent of the reduction reaction can easily be separated, recovered, and purified (if required) by a common method such as distillation. The unreacted raw material and solvent recovered can be reused (recycled) in the reaction.

The method of hydrolyzing the di(acetoxymethyl) cyclohexane is not particularly limited and any conventionally known method may be adopted. More specifically, for example, the hydrolysis may be carried out by a common method using an acidic or basic aqueous solution or a method in which the reaction with water is carried out using a solid acid or solid base such as an ion exchange resin as a hydrolyzing catalyst.

The reaction conditions of the hydrolysis are not particularly limited and a reaction temperature in a range of 30° C. to 160° C. is preferable and a range of 50° C. to 140° C. is most preferable. A reaction temperature below 30° C. may slow down the reaction rate significantly. On the other hand, a reaction temperature exceeding 160° C. may induce side reactions or the liquid phase of the reaction liquid may not be maintained.

By the above reaction, the target product cyclohexanedimethanol [$HOCH_2$—$C_6H_{10}$—$CH_2OH$] is obtained with the intermediate acetoxymethyl cyclohexanemethanol [$CH_3COOCH_2$—$C_6H_{10}$—$CH_2OH$] as a by-product. More specifically, when p-xylene is used as the starting material, 1,4-cyclohexanedimethanol is obtained with 4-acetoxymethyl cyclohexanemethanol as a by-product. To separate, recover, and purify (optional) the cyclohexanedimethanol and acetoxymethyl cyclohexanemethanol from the reaction liquid, common methods such as distillation and crystallization are adopted but are not particularly limited. The acetoxymethyl cyclohexanemethanol may be made into cyclohexanedimethanol by subjecting it again to the hydrolysis after separation, recovery, and purification.

On the other hand, the acetic acid which is generated as a by-product by the hydrolysis may be reused (recycled) as the raw material of the xylylene diacetate after separation, recovery, and purification (optional), i.e., in the oxidative acetoxylation reaction with xylene.

The following describes a producing method of cyclohexanedimethanol from xylylene diacetate via xylylene glycol.

The method of hydrolyzing the xylylene diacetate is not particularly limited and any conventionally known method may be used. More specifically, for example, hydrolysis may be carried out by a common method, as with the hydrolysis of the di(acetoxymethyl)cyclohexane. The reaction conditions of the hydrolysis of the xylylene diacetate may be the same as the reaction conditions of the hydrolysis of the di(acetoxymethyl)cyclohexane but are not particularly limited.

By the above reaction, xylylene glycol [$HOCH_2$—$C_6H_4$—$CH_2OH$] is obtained with the intermediate acetoxymethylbenzyl alcohol [$CH_3COOCH_2$—$C_6H_4$—$CH_2OH$] as a by-product. More specifically, when p-xylene is used as the starting material, p-xylylene glycol is obtained with 4-acetoxymethylbenzyl alcohol as a by-product. To separate, recover, and purify (optional) the xylylene glycol and acetoxymethylbenzyl alcohol from the reaction liquid, common methods such as distillation and crystallization are adopted but the method of separation, recovery, and purification is not particularly limited. The xylylene glycol after separation, recovery, and purification is fed to a reaction of a later stage. The acetoxymethylbenzyl alcohol may be made into the xylylene glycol by subjecting it again to the hydrolysis after separation, recovery, and purification.

On the other hand, the acetic acid which is generated as a by-product of the hydrolysis may be reused (recycled) as the raw material of the xylylene diacetate after separation, recovery, and purification (optional), i.e., in the oxidative acetoxylation reaction with xylene.

That is, the xylylene glycol is fed to a reaction of a later stage after separating it from the acetyl group containing compounds such as acetic acid, xylylene diacetate, acetoxymethylbenzyl alcohol, and acetoxymethyl benzoic acid, and the acetyl group containing compounds are recycled (optional) in their corresponding processes such as hydrolysis and oxidative acetoxylation reaction.

However, to carry out the hydrogenation of a later stage using as the raw material the xylylene glycol obtained by the hydrolysis, it is preferable that the amount (total amount) of acetyl group containing compounds such as acetic acid, xylylene diacetate, acetoxymethylbenzyl alcohol, and acetoxymethyl benzoic acid contained in the xylylene glycol is adjusted to not more than 10 weight %, and more preferably in a range of 10 ppm to 5 weight %, and further preferably 100 ppm to 5 weight %. When the xylylene glycol with the content (residual amount) of the acetyl group containing compounds exceeding 10 weight % is used as the raw material, the yield of the target product cyclohexanedimethanol is significantly reduced. Meanwhile, to make the content of the acetyl group containing compounds less than 10 ppm, i.e., to obtain xylylene glycol with the purity of 100% by removing essentially all the acetyl group containing compounds, for example, the number of theoretical plates of a distillation column needs to be increased when carrying out purification by the distillation method, or recrystallization needs to be carried out repeatedly when carrying out purification by the crystallization method, and as a result the size of the apparatus or the time required may be increased. Accordingly, cyclohexanedimethanol may not be produced inexpensively.

The method of hydrogenating the benzene ring of the xylylene glycol is not particularly limited and any conventionally known method may be adopted. More specifically, for example, the hydrogenation can be carried out by a common method, as with the hydrogenation of the benzene ring of the xylylene diacetate. The reaction conditions of the hydrogenation of the benzene ring of the xylylene glycol may be the same as the reaction conditions of the hydrogenation of the benzene ring of the xylylene diacetate but are not particularly limited.

By the above reaction, the target product cyclohexanedimethanol is obtained. Note that, the xylylene glycol, other than its use as the raw material of the cyclohexanedimethanol in accordance with the present invention, is an industrially highly useful material as the raw material of synthetic fibers and synthetic resin (particularly, heat resistant polymers), and thermoplastic materials, or as the raw material used to make a composite material of polyurethane and carbon fiber, etc.

With the producing method of the cyclohexanedimethanol in accordance with the present invention, it is possible to produce cyclohexanedimethanol at low cost in industrial applications, which is an industrially highly useful compound as a raw material of polyester paint and synthetic fibers, synthetic resins, and the like, using xylene as a starting material, which is inexpensive and readily available in industry. More specifically, when p-xylene is used as the starting material, 1,4-cyclohexanedimethanol can be produced at low cost in industrial applications.

The producing method of alcohols in accordance with the present invention is the method of producing alcohols having General Formula [1], in which a benzene ring of benzyl ester having General Formula [2] is hydrogenated, and then the resultant ester having General Formula [3] is hydrolyzed.

Further, the producing method of alcohols in accordance with the present invention is the method of producing alcohols having General Formula [1], in which benzyl ester having General Formula [2] is hydrolyzed, and then a benzene ring of the resultant benzyl alcohol having General Formula [4] is hydrogenated.

Furthermore, the producing method of alcohols in accordance with the present invention is the method of producing alcohols having General Formula [1], in which after adjusting the amount of acetyl group containing compounds contained in benzyl alcohol having General Formula [4] to not more than 10 weight %, a benzene ring of the benzyl alcohol is hydrogenated.

Further, the producing method of benzyl alcohols in accordance with the present invention is the method of producing benzyl alcohols having General Formula [4], in which after allowing the carboxylic acid represented by $R^3COOH$ to react in the presence of oxygen with a benzyl compound having General Formula [5] using a catalyst which includes palladium, gold ultra fine particles, and at least one kind of element selected from the group consisting of Group IIA, IIIA, VIA, IIB, VB, and VIII of the periodic table, and alkali metal, the resultant benzyl ester having General Formula [2] is hydrolyzed.

The benzyl ester used to produce the alcohols and benzyl alcohols is obtained, for example, by the reaction (oxidative esterification reaction) between a benzyl compound such as xylene or toluene and carboxylic acid such as acetic acid or (meta)acrylic acid in the presence of oxygen and a catalyst including palladium, gold ultra fine particles, and at least one kind of element selected from the group consisting of Group IIA, IIIA, VIA, IIB, VB, and VIII of the periodic table, and alkali metal.

The benzyl compound is not particularly limited and may be any compound which includes a benzyl group within a molecule, as in General Formula [5].

In General Formula [5], $R^1$ and $R^2$ independently represent a hydrogen atom or alkyl group, and X is a hydrogen atom, alkyl group, aryl group, hydroxy group, halogen group, nitro group, amino group, amido group, alkyloxy group, aryloxy group, carboxyl group including an alkylcarboxyl group and arylcarboxyl group, alkyl carbonyl group, arylcarbonyl group, or carboxyalkyl group including an alkylcarboxyalkyl group and arylcarboxyalkyl group. Basically, X may be any group as long as it does not play a role in the reactions in accordance with the present invention.

In General Formula [5], m is an integer of 1 to 6 which indicates the number of $(CR^1R^2H)$ groups, and n is an integer of 0 to 5 which indicates the number of X, where m+n=6.

More specifically, the benzyl compound includes, for example, alkyl benzene such as toluene, ethyl benzene, n-propyl benzene, isopropyl benzene, n-butyl benzene, sec-butyl benzene, and trimethyl benzene; o-, m-, p-dialkyl benzene such as xylene, ethyl toluene, n-propyl toluene, isopropyl toluene, n-butyl toluene, and sec-butyl toluene; aryl substituted alkyl benzene such as 4,4'-dimethylbiphenyl; o-, m-, p-hydroxy substituted alkyl benzene such as cresol; o-, m-, p-halogen substituted alkyl benzene such as chlorotoluene; nitro substituted alkyl benzene such as o-, m-, p-nitrotoluene; o-, m-, p-amino substituted alkyl benzene such as methylaniline; o-, m-, p-amido substituted alkyl benzene such as methylbenzamido; o-, m-, p-alkyloxy substituted alkylbenzene such as methylanisole; o-, m-, p-aryloxy substituted alkyl benzene such as phenoxy toluene; o-, m-, p-carboxy substituted alkyl benzene (tolyl carboxylate) such as tolyl acetate, tolyl propionate, tolyl butanoate, tolyl benzoate; o-, m-, p-carbonyl substituted alkyl benzene such as methylacetophenone and methylbenzophenone; and o-, m-, p-carboxyalkyl substituted alkylbenzene such as methylbenzyl acetate. Of these benzyl compounds as exemplified above, alkylbenzene, dialkylbenzene, and carboxyalkyl substituted alkylbenzene are more preferable, and toluene and o-, m-, p-xylene are particularly preferable.

Note that, it is deemed that the benzyl compound in accordance with the present invention includes compounds having a condensed ring or heterocyclic ring, instead of the benzene ring (benzyl group) as in General Formula [5], and specifically, for example, compounds such as methyl naphthalene and dimethyl pyridine.

The carboxylic acid used in the reaction with the benzyl compound is not particularly limited as long as it is represented by $R^3COOH$. In the formula, $R^3$ is a group having a benzene ring, or an alkyl, alkenyl, or alkynyl group with 1 to 6 carbon atoms.

As the carboxylic acids, monocarboxylic acids are preferable. Specifically, for example, the following compounds but not limited to these are available: aliphatic carboxylic acid such as acetic acid, acrylic acid, methacrylic acid, propionic acid, and butanoic acid, and aromatic carboxylic acid such as benzoic acid (with or without a substituent). Of these carboxylic acids as exemplified above, acetic acid, acrylic acid, and methacrylic acid are preferable. When acrylic acid or methacrylic acid is used, a benzyl ester having a double bond, which can be easily polymerized can be obtained.

The mole ratio of the carboxylic acid with respect to the benzyl group of the benzyl compound is to be larger than the stoichiometric ratio and is not particularly limited, but a range of 1:1 to 20:1 is more preferable. When the mole ratio is below 1:1, the carboxylic acid will be deficient, and the benzyl ester as the ester may not be produced efficiently. On the other hand, even when the carboxylic acid is used at a mole ratio which exceeds 20:1, a further improvement in yield, etc., cannot be expected as compared with the mole ratio in the above range. In fact, in such a case, since the carboxylic acid is used in a large amount, it might increase the size of the reaction apparatus and the recovering device for recovering the excess carboxylic acid, thus possibly increasing the production cost, including the recovering cost.

The catalyst used in the reaction between the benzyl compound and the carboxylic acid may be the same as the catalyst used in the oxidative acetoxylation reaction between the xylene and acetic acid, and the preparation method and the method of using the catalyst are as described above.

By the oxidative esterification reaction between the benzyl compound and carboxylic acid in the presence of the catalyst, the benzyl ester in accordance with the present invention is obtained. The oxidation reaction is carried out in a liquid phase or gaseous phase in the presence of an oxygen gas (molecular oxygen). That is, in the present invention, the oxidation reaction may be carried out in a liquid phase or gaseous phase but the liquid phase is more preferable. The oxygen gas may be diluted with an inert gas such as nitrogen gas, helium gas, or argon gas. Further, air may be used as the gas containing oxygen. The supply method of the oxygen gas into the reaction system is not particularly limited.

The oxidation reaction may be any of a continuous type, batch type, and semibatch type, and is not particularly limited. For example, when the reaction is of a batch type, the catalyst is fed to the reaction apparatus together with the raw material, and in the case of a continuous type, for example, the catalyst is introduced into the reaction apparatus in advance, or it is fed to the reaction apparatus continuously with the raw material. Thus, the catalyst may be used in any of a fixed bed, fluidized bed, and suspension bed.

The amount of catalyst used with respect to the benzyl compound is not particularly limited, and it is set in accordance with types and combination of the benzyl compound and carboxylic acid, the composition of the catalyst, and reaction conditions, etc.

Reaction conditions such as reaction temperature, reaction pressure, and reaction time are not particularly limited, and they are set in accordance with types and combination of the benzyl compound and carboxylic acid, and the composition of the catalyst, etc., and a reaction temperature in a range of 80° C. to 200° C. is preferable. A reaction temperature below 80° C. slows down the reaction rate and the benzyl ester may not be synthesized. efficiently. On the other hand, a reaction temperature exceeding 200° C. facilitates side reactions including combustion and the benzyl ester may not be synthesized efficiently. Further, corrosion of the reaction apparatus by the carboxylic acid may be induced.

The reaction pressure is not particularly limited and may be either of reduced pressure, ordinary pressure (atmospheric pressure) and applied pressure, and when using an oxygen gas (undiluted oxygen gas) in the oxidation reaction, a pressure in a range of ordinary pressure ($1.0 \times 10^5$ Pa) to $4.9 \times 10^6$ Pa (gauge pressure) is preferable, and when using air in the oxidation reaction, a pressure in a range of ordinary pressure to $9.8 \times 10^6$ pa (gauge pressure) is preferable. A reaction pressure exceeding $9.8 \times 10^6$ pa is not preferable from an industry stand point such as reaction equipment, etc.

Note that, the oxidation reaction does not particularly require a solvent when the benzyl compound and/or carboxylic acid are liquid under the above reaction condition. However, when these compounds cannot be uniformly mixed together, or when the reaction is violent, the reaction liquid may be diluted with a solvent which is inactive toward the reaction.

The benzyl ester obtained by the above method, for example, such as p-methylbenzyl acetate and p-xylylene diacetate, is a compound suitable as a raw material of synthetic resin such as polyester resin, as various chemical agents such as perfume and solvent, or as a raw material of such chemical agents. Note that, the method of separating, recovering, and purifying the benzyl ester is not particularly limited.

The target product alcohols having General Formula [5] are produced by hydrogenating the benzene ring of the benzyl ester synthesized by the above method and then by hydrolyzing the resultant esters having General Formula [3]. Further, by hydrolyzing the benzyl ester synthesized by the above method, the target product benzyl alcohols having General Formula [4] are produced, and by hydrogenating the benzene ring of the benzyl alcohols, the target product alcohols having General Formula [5] are produced.

The following describes a producing method of alcohols from benzyl esters via esters.

The method of hydrogenating the benzene ring of the benzyl ester is not particularly limited and any conventionally known method may be adopted. More specifically, the hydrogenation can be carried out, for example, by a common method of the reaction with hydrogen using a reducing catalyst such as (i) a noble metal supporting catalyst in which a noble metal (Pt group) such as palladium, platinum, ruthenium, rhodium, or iridium is immobilized on a support such as active carbon, alumina, or diatomaceous earth, (ii) a noble metal oxide such as palladium oxide, platinum oxide, ruthenium oxide, rhodium oxide, or iridium oxide, (iii) a noble metal simple substance such as palladium black, platinum black, ruthenium black, or rhodium black; (iv) a Raney catalyst such as Raney nickel, Raney cobalt, Raney ruthenium; and (v) a base metal supporting catalyst supporting a base metal on a support.

Note, however, that when the benzyl ester obtained by the oxidative esterification reaction between the benzyl compounds and carboxylic acids is used as the raw material to carry out the hydrogenation, in view of the yield of the target product and the cost, it is preferable to hydrogenate the benzene ring of the benzyl ester after adjusting the content of the acetic acid, acrylic acid, or carboxylic acid such as methacrylic acid included in the benzyl ester to not more than 10 weight %.

Hydrogen is used in excess of the benzyl ester. Thus, the mole ratio of hydrogen with respect to the benzyl ester, and the supply method of hydrogen are not particularly limited. Further, the amount of reducing catalyst used with respect to the benzyl ester is set in accordance with the composition of the reducing catalyst, reaction conditions, and the supply method of hydrogen, etc., and is not particularly limited. Reaction conditions such as reaction temperature, reaction pressure, and reaction time are set in accordance with the composition and the amount of reducing catalyst used and the supply method of hydrogen, etc., and are not particularly limited but a reaction temperature of ordinary temperature to 250° C. is preferable and 50° C. to 200° C. is most preferable. A reaction temperature below ordinary temperature (25° C.) may slow the reaction rate significantly. On the other hand, a reaction temperature exceeding 250° C. may induce side reactions more often. Further, the reaction pressure is preferably an applied pressure. Note that, the hydrogenation reaction may not necessarily require a solvent but may be diluted as required using a solvent which is inactive toward the reaction.

By the above reaction, esters having General Formula [3] are obtained. Note that, the esters are fed to a reaction of the following stage after filtering out the reducing catalyst.

The catalyst used in the reduction reaction is easily separated and recovered from the reaction liquid by common methods such as filtration and distillation. Further, the resultant product, unreacted raw material, and solvent of the reduction reaction can easily be separated, recovered, and purified (if required) by a common method such as distillation. The unreacted raw material and solvent recovered can be reused (recycled) in the reaction.

The method of hydrolyzing the esters is not particularly limited and any conventionally known method may be adopted. More specifically, for example, the hydrolysis may be carried out by a common method using an acidic or basic aqueous solution or a method in which the reaction with water is carried out using a solid acid or solid base such as an ion exchange resin as a hydrolyzing catalyst.

The reaction conditions of the hydrolysis are not particularly limited and a reaction temperature in a range of 30° C. to 160° C. is preferable and a range of 50° C. to 140° C. is most preferable. A reaction temperature below 30° C. may slow down the reaction rate significantly. On the other hand, a reaction temperature exceeding 160° C. may induce side reactions or the liquid phase of the reaction liquid may not be maintained.

By the above reaction, the target product alcohols are obtained. To separate, recover, and purify (optional) the alcohols from the reaction liquid, common methods such as distillation and crystallization are adopted but the method of separation, recovery, and purification is not particularly limited.

On the other hand, the carboxylic acid such as acetic acid, acrylic acid, or methacrylic acid which is generated as a by-product by the hydrolysis may be reused (recycled) as the raw material of the benzyl ester after separation, recovery, and purification (optional), i.e., in the oxidative esterification reaction with the benzyl compound.

The following describes a producing method of benzyl alcohols by the hydrolysis of the benzyl ester, and a producing method of alcohols by the hydrogenation of a benzene ring of the benzyl alcohols.

The method of hydrolyzing the benzyl ester is not particularly limited and any conventionally known method may be used. More specifically, for example, hydrolysis may be carried out by a common method, as with the hydrolysis of the esters. The reaction conditions of the hydrolysis of the benzyl ester may be the same as the reaction conditions of the hydrolysis of the esters but are not particularly limited.

By the above reaction, the target product benzyl alcohols are obtained. To separate, recover, and purify (optional) the target product benzyl alcohols from the reaction liquid, common methods such as distillation and crystallization are adopted but the method of separation, recovery, and purification is not particularly limited.

On the other hand, the carboxylic acid such as acetic acid, acrylic acid, or methacrylic acid which is generated as a by-product of the hydrolysis may be reused (recycled) as the raw material of the benzyl ester after separation, recovery, and purification (optional), i.e., in the oxidative esterification reaction.

That is, when further producing alcohols from the benzyl alcohols after separating it from acetyl group containing compounds such as acetic acid, xylylene diacetate, acetoxymethylbenzyl alcohol, and acetoxymethyl benzoic acid, the benzyl alcohols are fed to a reaction of a later stage, and the acetyl group containing compounds are recycled (optional) in their corresponding processes such as hydrolysis and oxidative esterification reaction.

However, to carry out the hydrogenation of a later stage using as the raw material the benzyl alcohols obtained by the hydrolysis, it is preferable that the amount (total amount) of acetyl group containing compounds such as acetic acid, xylylene diacetate, acetoxymethylbenzyl alcohol, and acetoxymethyl benzoic acid contained in the benzyl alcohols is adjusted to not more than 10 weight %, and more preferably in a range of 10 ppm to 5 weight %, and further preferably 100 ppm to 5 weight %. When the benzyl alcohols with the content (residual amount) of the acetyl group containing compounds exceeding 10 weight % is used as the raw material, the yield of the target product alcohols is significantly reduced. Meanwhile, to make the content of the acetyl group containing compounds less than 10 ppm, i.e., to obtain benzyl alcohols with the purity of 100% by removing essentially all the acetyl group containing compounds, for example, the number of theoretical plates of a distillation column needs to be increased when carrying out purification by the distillation method, or recrystallization needs to be carried out repeatedly when carrying out purification by the crystallization method, and as a result the size of the apparatus or the time required may be increased. Accordingly, alcohols may not be produced at low cost.

The method of hydrogenating the benzene ring of the benzyl alcohols is not particularly limited and any conventionally known method may be adopted. More specifically, for example, the hydrogenation can be carried out by a common method, as with the hydrogenation of the benzene ring of the benzyl ester. The reaction conditions of the hydrogenation of the benzene ring of the benzyl alcohols may be the same as the reaction conditions of the benzene ring of the benzyl ester but are not particularly limited.

By the above reaction, the target product alcohols are obtained.

With the producing method of alcohols and benzyl alcohols in accordance with the present invention, it is possible to produce alcohols such as benzyl alcohols at low cost in industrial applications, which is an industrially highly useful compound, using benzyl compounds such as toluene or xylene as a starting material, which are inexpensive and readily available in industry.

For example, when p-xylene is used as the starting material, 1,4-cyclohexanedimethanol, as well as p-xylylene glycol, 4-methylcyclohexylmethanol, and p-methylbenzyl alcohol can be produced at low cost in industrial applications. Further, when toluene is used as the starting material, cyclohexyl methanol and benzyl alcohol can be produced at low cost in industrial applications.

EXAMPLES

The following will describe the present invention in more detail by way of Examples and Comparative Examples but the present invention is not to be limited in any ways by the following. Note that, "turnover frequency" (TOF) in Examples relates to a measure of productivity of a catalyst, which is defined by the following.

TOF=[(mole number of methylbenzyl acetate generated)]+2(mole number of xylylene diacetate generated)/[mole number of palladium contained in a catalyst×reaction time (time)]

Example 1

0.22 g of tetrachloroauric (III) acid.4 hydrate as a gold compound was dissolved in 200 ml of water, and after heating to 60° C., the pH was adjusted to 8.5 using an aqueous solution of sodium hydroxide, thus preparing an aqueous solution of tetrachloroauric (III) acid. Then, 62 mg of tetraammine palladium dichloride as a palladium compound and 0.2 g of sodium laurate as a surfactant were added to the aqueous solution and were dissolved therein. To the aqueous solution thus obtained was added 5 g of titanium oxide (provided by Norton K.K.) as a support at 60° C., and the mixture was stirred for an hour at the same temperature to suspend the titanium oxide and to immobilize a palladium precipitate and gold precipitate on the surface of the suspended titanium oxide.

Thereafter, the suspension liquid was filtered, and the filter cake, i.e., the palladium-gold precipitate immobilized product was water washed and was dried for 8 hours at 120° C. Then, the palladium-gold precipitate immobilized product was calcined in air for 3 hours at 400° C. to obtain a titanium oxide supported palladium-gold (super fine particles) as gold ultra fine particles immobilized product. The aqueous solutions before and after the preparation of the titanium oxide supported palladium-gold were taken for an X-ray fluorescence analysis, and it was found that the supported amount (content) of palladium and the supported amount (content) of gold in the titanium oxide supported palladium-gold were 0.5 weight % and 2.0 weight %, respectively. Also, the particle size of the metal supported on the titanium oxide was in a range of 5 nm to 10 nm.

Then, to a 300 ml rotary autoclave were added 3.0 g of the titanium oxide supported palladium-gold prepared (palladium content of 0.14 mmole), 60 mg of bismuth acetate oxide, and 0.6 g of potassium acetate. That is, the catalyst in accordance with the present invention was prepared by mixing these compounds, etc.

Then, the autoclave was sealed after adding 30 g of p-xylene and 36 g of acetic acid. Thereafter, air was drawn into the autoclave, and after increasing the internal pressure to $9.81 \times 10^5$ Pa (gauge pressure), the autoclave was heated to 140° C. to allow an oxidative acetoxylation reaction for 2 hours with stirring at 700 rpm. Note that, because the oxygen gas inside the autoclave is consumed as the reaction proceeds, an oxygen gas was appropriately added during reaction to maintain the internal pressure of $9.81 \times 10^5$ Pa.

After the reaction was finished, the contents were taken out of the autoclave and filtered, and after removing the catalyst, the composition of the reaction liquid was analyzed by gas chromatography. The analysis revealed that the reaction liquid contained 10.05 g of 4-methylbenzyl acetate and 6.30 g of p-xylylene diacetate, and the conversion of p-xylene was 36.9 mole %. Thus, the yield of 4-methylbenzyl acetate with respect to p-xylene was 21.9 mole %, and the yield of p-xylylene diacetate was 10.6 mole %. The results showed that the turnover frequency per unit time with respect to per unit palladium of the catalyst was 398.

Then, to a 100 ml autoclave were added 5 g of the p-xylylene diacetate, 20 g of water, and 10 g of methyl alcohol, and the autoclave was sealed after adding 1.0 g of active carbon supported ruthenium as the reducing catalyst (ruthenium content of S weight %). Thereafter, after replacing inside the autoclave by nitrogen gas, hydrogen gas was drawn into the autoclave and the pressure inside the autoclave was increased to $4.9 \times 10^6$ Pa. Then, the autoclave was heated to 100° C. and a reaction was allowed while stirring until there was no further absorption of hydrogen (until there was no further decrease in internal pressure).

After the reaction was finished, the contents were taken out of the autoclave and filtered, and after removing the reducing catalyst, the composition of the reaction liquid was analyzed by gas chromatography. The analysis revealed that the reaction liquid contained 3.37 g of 1,4-di(acetoxymethyl)cyclohexane and the conversion of p-xylylene diacetate was 100 mole %. Thus, the yield of 1,4-di(acetoxymethyl)cyclohexane with respect to p-xylylene diacetate was 66.0 mole %.

To a 50 ml round-bottom flask equipped with a reflux condenser were added altogether 3 g of the 1,4-di(acetoxymethyl)cyclohexane, 6 g of water, and 26 mg of p-toluene sulfonic acid as the hydrolyzing catalyst, and the mixture was stirred for 23 hours at 100° C.

After the reaction was finished, the contents were taken out and the hydrolyzing catalyst was removed, and the composition of the reaction liquid was analyzed by liquid chromatography. The analysis revealed that the reaction liquid contained 1.36 g of 1,4-cyclohexanedimethanol, 0.63 g of 4-acetoxymethyl cyclohexanemethanol, and the conversion of 1,4-di(acetoxymethyl)cyclohexane was 100%. Thus, the yield of 1,4-cyclohexanedimethanol with respect to 1,4-di(acetoxymethyl)cyclohexane was 72 mole %, and the yield of 4-acetoxymethyl cyclohexanemethanol was 26 mole %.

Example 2

To a 100 ml round-bottom flask equipped with a reflux condenser were added altogether 5 g of p-xylylene diacetate which was obtained in the same manner as in Example 1, 100 g of water, and 0.4 g of cation exchange resin (Dow-x 50 W H type, provided by The Dow Chemical Co.) as the hydrolyzing catalyst, and the mixture was stirred for 24 hours at 100° C.

After the reaction was finished, the contents were taken out and filtered, and after removing the hydrolyzing catalyst, water was removed from the reaction liquid using a rotary evaporator. The resultant (product) was distilled under the reduced pressure of 133 Pa at 140° C. This gave 2 g of p-xylylene glycol. By analysis, the p-xylylene glycol contained 100 ppm of p-acetoxymethylbenzyl alcohol (intermediate), which is the acetyl group containing compound.

Then, to a 50 ml autoclave were added 2 g of the p-xylylene glycol, 8 g of water, and 3 g of methyl alcohol, and the autoclave was sealed after adding 0.4 g of active carbon supported ruthenium (ruthenium content of 5 weight %) Thereafter, after replacing inside the autoclave by nitrogen gas, hydrogen gas was drawn into the autoclave and the pressure inside the autoclave was increased to $4.9 \times 10^6$ Pa. Then, the autoclave was heated to 100° C. and a reaction was allowed while stirring until there was no further absorption of hydrogen (until there was no further decrease in internal pressure).

After the reaction was finished, the contents were taken out of the autoclave and filtered, and after removing the reducing catalyst, the composition of the reaction liquid was analyzed by gas chromatography. The analysis revealed that the reaction liquid contained 1.54 g of 1,4-cyclohexanedimethanol, and the conversion of p-xylylene glycol was 100 mole %. Thus, the yield of 1,4-cyclohexanedimethanol with respect to p-xylylene glycol was 76 mole %.

Meanwhile, p-xylylene glycol which was obtained in the same manner as in the above method was treated with an aqueous solution of 10 weight % of sodium hydroxide, and water was evaporated to allow for crystal deposition, thereby obtaining 3 g of p-xylylene glycol which does not contain the acetyl group containing compound.

Using the p-xylylene glycol containing no impurities, the hydrogenation was performed under the same reaction conditions as above and the composition of the reaction liquid was analyzed. The analysis revealed that the reaction liquid contained 2.34 g of 1,4-cyclohexanedimethanol, and the conversion of p-xylylene glycol was 100 mole %. Thus, the yield of 1,4-cyclohexanedimethanol with respect to p-xylylene glycol was 74 mole %.

Comparative Example

After dissolving 0.22 g of tetrachloroauric (III) acid.4 hydrate and 62 mg of tetraammine palladium dichloride in 200 ml of water, 5 g of titanium oxide (provided by Norton K.K.) was added in the aqueous solution. Then, the mixture was heated to evaporate and deplete moisture. Thereafter, the immobilized palladium-gold precipitate was dried for 8 hours at 120° C. and calcined in air for 3 hours at 400° C., the palladium component and gold component were immobilized on the surface of the titanium oxide by the impregnation method to obtain a titanium oxide supported palladium-gold as a comparative catalyst. Thus, the gold supported on the titanium oxide is not in the form of ultra fine particles. The supported amount (content) of palladium and the supported amount (content) of gold in the comparative titanium oxide supported palladium-gold were 0.5 weight % and 2.0 weight %, respectively.

Then, to a 100 ml rotary autoclave were added 10 g of p-xylene and 12 g of acetic acid, and the autoclave was sealed after adding 1.0 g of the comparative titanium oxide supported palladium-gold. Thereafter, the oxidative acetoxylation reaction was performed under the same reaction conditions as in Example 1 and the composition of the reaction liquid was analyzed. The analysis revealed that essentially no p-methylbenzyl acetate and p-xylylene diacetate were contained in the reaction liquid. That is, the comparative catalyst had essentially no catalytic activity.

Comparative Example 2

1.35 g of bismuth nitrate.5 hydrate was added to 50 ml of water, and the aqueous solution was stirred while adding a small amount of nitric acid until the solid completely dissolved to prepare a homogeneous aqueous solution. After adding 5.0 g of a silica power (provided by Norton K.K.) to the aqueous solution, the mixture was heated to evaporate and deplete moisture. The solid product thus obtained was calcined in air for 2 hours at 500° C. to obtain a silica supported bismuth.

Then, 0.45 g of palladium chloride was added to 50 ml of water, and the aqueous solution was stirred while adding a small amount of hydrochloric acid until the solid completely dissolved at 60° C. to prepare a homogeneous aqueous solution. After adding the silica supported bismuth thus obtained to the aqueous solution, moisture was evaporated and depleted while stirring the mixture. After drying the immobilized palladium-bismuth product for 8 hours at 120° C., it was calcined in nitrogen gas for 2 hours at 400° C. and further calcined (hydrogenated) in hydrogen gas for 2 hours at 400° C. to obtain a silica supported palladium-bismuth as a comparative catalyst. Thus, the comparative catalyst contained no gold ultra fine particles. The supported amount of palladium in the comparative silica supported palladium-bismuth was 5.4 weight %.

Then, to a 100 ml rotary autoclave were added 5 g of xylene and 24 g of acetic acid, and the autoclave was sealed after adding 1.0 g of the comparative silica supported palladium-bismuth. Then, oxygen gas was drawn into the autoclave and the pressure therein was increased to 9.81×10⁵ Pa (gauge pressure), and by heating to 140° C., the oxidative acetoxylation reaction was allowed as in Example 1 for 5 hours while stirring at 700 rpm.

After the reaction was finished, the contents were taken out and filtered, and after removing the catalyst, the composition of the reaction liquid was analyzed by gas chromatography. The analysis revealed that the reaction liquid contained 0.17 g of 4-methylbenzyl acetate and 0.097 g of p-xylylene diacetate, and the conversion of 4-methylbenzyl acetate with respect to p-xylene was 1.9 mole % and the yield of p-xylylene diacetate was 0.9 mole %. Further, the results showed that the turnover frequency per unit time with respect to unit palladium of the catalyst was 0.7, thus finding a significantly low catalytic activity of the catalyst of the Comparative Example.

Example 3

To study influence of the acetyl group containing compound in hydrogenation, 1,4-cyclohexanedimethanol was produced using as a raw material 3 g of p-xylylene glycol with a purity of 95 weight %. The p-xylylene glycol contained 0.11 g of p-acetoxymethylbenzyl alcohol as the acetyl group containing compound, 0.032 g of p-xylylene diacetate, and 0.008 g of acetic acid (accordingly, 2.85 g of p-xylylene glycol).

Using the p-xylylene glycol containing these impurities, the hydrogenation was performed under the same reaction conditions as in Example 2 and the composition of the reaction liquid was analyzed. The analysis revealed that the reaction liquid contained 2.23 g of 1,4-cyclohexanedimethanol, and the conversion of p-xylylene glycol was 100 mole %. Thus, the yield of 1,4-cyclohexanedimethanol with respect to p-xylylene glycol was 75 mole %.

Example 4

To study influence of the acetyl group containing compound in hydrogenation, 1,4-cyclohexanedimethanol was produced, using as a raw material 3 g of p-xylylene glycol with the purity of 98 weight %. The p-xylylene glycol contained 0.05 g of p-acetoxymethylbenzyl alcohol as the acetyl group containing compound and 0.02 g of p-xylylene diacetate (accordingly, 2.93 g of p-xylylene glycol).

Using the p-xylylene glycol having these impurities, the hydrogenation was performed under the same reaction conditions as in Example 2, and the composition of the reaction liquid was analyzed. The analysis revealed that the reaction liquid contained 2.24 g of 1,4-cyclohexanedimethanol, and the conversion of p-xylylene glycol was 100 mole %. Thus, the yield of 1,4-cyclohexanedimethanol with respect to p-xylylene glycol was 73.4 mole %.

Comparative Example 3

To study influence of the acetyl group containing compound in hydrogenation, 1,4-cyclohexanedimethanol was produced using as a raw material 3 g of p-xylylene glycol with a purity of less than 90 weight %. The p-xylylene glycol contained 0.17 g of p-acetoxymethylbenzyl alcohol as the acetyl group containing compound, 0.10 g of p-xylylene diacetate, and 0.04 g of acetic acid (accordingly, 2.69 g of p-xylylene glycol).

Using the p-xylylene glycol having these impurities, the hydrogenation was performed under the same reaction conditions as in Example 2 and the composition of the reaction liquid was analyzed. The analysis revealed that the reaction liquid contained 1.83 g of 1,4-cyclohexanedimethanol, and the conversion of p-xylylene glycol was 100 mole %. Thus, the yield of 1,4-cyclohexanedimethanol with respect to p-xylylene glycol was 65 mole %.

Example 5

0.22 g of tetrachloroauric (III) acid.4 hydrate as a gold compound was dissolved in 200 ml of water, and after heating to 60° C., the pH was adjusted to 8.5 using an aqueous solution of sodium hydroxide, thus preparing an aqueous solution of tetrachloroauric (III) acid. Then, 62 mg of tetraammine palladium dichloride as a palladium compound and 0.2 g of sodium laurate as a surfactant were added to the aqueous solution and were dissolved therein. To the aqueous solution thus obtained was added 5 g of titanium oxide (provided by Norton K.K.) as a support at 60° C., and the mixture was stirred for an hour at the same temperature to suspend the titanium oxide and to immobilize a palladium precipitate and gold precipitate on the surface of the suspended titanium oxide.

Thereafter, the suspension liquid was filtered, and the filter cake, i.e., the immobilized palladium-gold precipitate was water washed and was dried for 8 hours at 120° C. Then, the immobilized palladium-gold precipitate was calcined in air for 3 hours at 400° C. to obtain a titanium oxide supported palladium-gold (super fine particles) as immobilized gold ultra fine particles. The aqueous solutions before and after the preparation of the titanium oxide supported palladium-gold were taken for an X-ray fluorescence analysis, and it was found that the supported amount of palladium and the supported amount of gold in the titanium oxide supported palladium-gold were 0.5 weight % and 2.0 weight %, respectively. Also, the particle size of the metal supported on the titanium oxide was in a range of 5 nm to 10 nm.

Then, to a 300 ml rotary autoclave were added 3.0 g of the titanium oxide supported palladium-gold prepared (palladium content of 0.14 mmole), 60 mg of bismuth acetate oxide, and 0.6 g of potassium acetate. That is, the catalyst in accordance with the present invention was prepared by mixing these compounds, etc. in the autoclave.

Then, the autoclave was sealed after adding 30 g of p-xylene and 36 g of acetic acid. Thereafter, air was drawn into the autoclave, and after increasing the internal pressure to $9.81 \times 10^5$ Pa (gauge pressure), the autoclave was heated to 140° C. to allow an oxidative acetoxylation reaction for 2 hours with stirring at 700 rpm. Note that, because the oxygen gas inside the autoclave is consumed as the reaction proceeds, oxygen gas was appropriately added during reaction to maintain the internal pressure of $9.81 \times 10_5$ Pa.

After the reaction was finished, the contents were taken out of the autoclave and filtered, and after removing the catalyst, the composition of the reaction liquid was analyzed by gas chromatography. The analysis revealed that the reaction liquid contained 10.05 g of 4-methylbenzyl acetate and 6.30 g of p-xylylene diacetate, and the conversion of p-xylene was 36.9 mole %. Thus, the yield of 4-methylbenzyl acetate with respect to p-xylene was 21.9 mole %, and the yield of p-xylylene diacetate was 10.6 mole %. The results showed that the turnover frequency per unit time with respect to per unit palladium of the catalyst was 398.

Then, to a 100 ml autoclave were added 5 g of the 4-methylbenzyl acetate, 20 g of water, and 10 g of methyl alcohol, and the autoclave was sealed after adding 1.0 g of active carbon supported ruthenium as the reducing catalyst (ruthenium content of 5 weight %). Thereafter, after replacing inside the autoclave by nitrogen gas, hydrogen gas was drawn into the autoclave and the pressure inside the autoclave was increased to $9.8 \times 10^6$ Pa. Then, the autoclave was heated to 50° C. and a reaction was allowed while stirring until there was no further absorption of hydrogen (until there was no further decrease in internal pressure).

After the reaction was finished, the contents were taken out of the autoclave and filtered, and after removing the catalyst, the composition of the reaction liquid was analyzed by gas chromatography. The analysis revealed that the reaction liquid contained 4.25 g of 4-acetoxymethyl cyclohexylmethanol and the conversion of 4-acetoxymethyl cyclohexylmethanol was 100 mole %. Thus the yield of 4-acetoxymethyl cyclohexylmethanol with respect to 4-methylbenzyl acetate was 82.0 mole %.

To a 50 ml round-bottom flask equipped with a reflux condenser were added altogether 3 g of the 4-acetoxymethyl cyclohexylmethanol, 6 g of water, and 26 mg of p-toluene sulfonic acid as the hydrolyzing catalyst, and the mixture was stirred for 8 hours at 100° C.

After the reaction was finished, the contents were taken out and the hydrolyzing catalyst was removed, and the composition of the reaction liquid was analyzed by liquid chromatography. The analysis revealed that the reaction liquid contained 1.87 g of 4-methyl cyclohexylmethanol, and the conversion of 4-acetoxymethyl cyclohexylmethanol was 83 mole %. Thus, the yield of 4-acetoxylmethyl cyclohexylmethanol was 83 mole %.

Example 6

To a 100 ml round-bottom flask equipped with a reflux condenser were added altogether 5 g of 4-methylbenzyl acetate which was obtained in the same manner as in Example 5, 100 g of water, and 0.4 g of cation exchange resin (Dow-x 50 W H type, provided by The Dow Chemical Co.) as the hydrolyzing catalyst, and the mixture was stirred for 6 hours at 100° C.

After the reaction was finished, the contents were taken out and filtered, and after removing the hydrolyzing catalyst, water was removed from the reaction liquid using a rotary evaporator. The resultant (product) was distilled under the reduced pressure of 2133 Pa at 102° C. This gave 3.1 g of p-methylbenzyl alcohol. By analysis, the p-methylbenzyl alcohol contained 100 ppm of 4-methylbenzyl acetate (raw material), which is the acetyl group containing compound.

Then, to a 30 ml autoclave were added 2 g of the methylbenzyl alcohol, 10 g of water, and 0.16 ml of 1N sodium hydroxide, and the autoclave was sealed after adding 0.16 g of active carbon supported ruthenium (ruthenium content of 5 weight %). Thereafter, inside the autoclave was replaced with nitrogen gas, followed by hydrogen gas. After having replaced with hydrogen gas, the hydrogen pressure therein was increased to $10.8 \times 10^6$ Pa to $12.7 \times 10^6$ Pa at 45° C. to 90° C., and a reaction was allowed for 8 hours.

After the reaction was finished, the contents were taken out of the autoclave and filtered, and after removing the reducing catalyst, the composition of the reaction liquid was analyzed by gas chromatography. The analysis revealed that the reaction liquid contained 1.91 g of 4-methylcyclohexyl methanol, and the conversion of p-methylbenzyl alcohol was 100 mole %. Thus, the yield of 4-methylcyclohexyl alcohol with respect to p-methylbenzyl alcohol was 91 mole %.

Example 7

First, after preparing the catalyst as in Example 5, 9.1 g of toluene and 23.8 g of acetic acid were added to a 100 ml rotary autoclave and the autoclave was sealed. Then, a nitrogen gas was drawn into the autoclave to increase the pressure therein to $2.0 \times 10^6$ Pa (gauge pressure), and the autoclave was heated to 140° C. with stirring at 700 rpm. After increasing the temperature, the pressure inside the autoclave was adjusted by nitrogen gas to $2.45 \times 10^6$ Pa (gauge pressure). The pressure was further increased by oxygen gas to $3.0 \times 10^6$ Pa and the oxidative acetoxylation reaction was allowed for 2 hours. Note that, because the oxygen gas inside the autoclave is consumed as the reaction proceeds, oxygen gas was appropriately added during reaction to maintain the internal pressure of $3.0 \times 10^6$ Pa.

After the reaction was finished, the contents were taken out of the autoclave and filtered, and after removing the catalyst, the composition of the reaction liquid was analyzed by gas chromatography. The analysis revealed that the reaction liquid contained 6.71 g of benzyl acetate and the conversion of toluene was 51.2 mole %. Thus, the yield of benzyl acetate with respect to toluene was 45.1 mole %. The results showed that the turnover frequency per unit time with respect to per unit palladium of the catalyst was 941.

Then, to a 100 ml autoclave were added 5 g of the benzyl acetate synthesized by the above method, 20 g of water, and 10 g of methyl alcohol, and the autoclave was sealed after adding 1.0 g of active carbon supported ruthenium as the reducing catalyst (ruthenium content of 5 weight %). Thereafter, after replacing inside the autoclave by nitrogen gas, hydrogen gas was drawn into the autoclave and the pressure inside the autoclave was increased to $9.8 \times 10^6$ Pa. Then, the autoclave was heated to 50° C. and a reaction was allowed while stirring until there was no further absorption of hydrogen (until there was no further decrease in internal pressure).

After the reaction was finished, the contents were taken out of the autoclave and filtered, and after removing the reducing catalyst, the composition of the reaction liquid was analyzed by gas chromatography. The analysis revealed that the reaction liquid contained 3.43 g of acetoxymethyl cyclohexane and the conversion of benzyl acetate was 100 mole %. Thus, the yield of acetoxymethyl cyclohexane with respect to benzyl acetate was 66.0 mole %.

Then, to a 50 ml round-bottom flask equipped with a reflux condenser were added altogether 3 g of the acetoxymethyl cyclohexane, 6 g of water, and 26 mg of p-toluene sulfonic acid as the hydrolyzing catalyst, and the mixture was stirred for 4 hours at 100° C.

After the reaction was finished, the contents were taken out and the hydrolyzing catalyst was removed, and the composition of the reaction liquid was analyzed by liquid chromatography. The analysis revealed that the reaction liquid contained 1.82 g of cyclohexylmethanol, and the conversion of acetoxymethyl cyclohexane was 87 mole %. Thus, the yield of cyclohexyl methanol was 87 mole %.

Example 8

To a 100 ml round-bottom flask equipped with a reflux condenser were added altogether 5 g of benzyl acetate which was obtained in the same manner as in Example 7, 100 g of water, and 0.4 g of cation exchange resin (Dow-x 50 W H type, provided by The Dow Chemical Co.) as the hydrolyzing catalyst, and the mixture was stirred for 6 hours at 100° C.

After the reaction was finished, the contents were taken out and filtered, and after removing the hydrolyzing catalyst, water was removed from the reaction liquid using a rotary evaporator. The resultant (product) was distilled under the reduced pressure of 1333 Pa at 95° C. This gave 2.5 g of benzyl alcohol. By analysis, the benzyl alcohol contained 80 ppm of benzyl acetate (raw material), which is the acetyl group containing compound.

Then, to a 30 ml autoclave were added 2 g of the benzyl alcohol, 10 g of water, and 0.16 ml of 1N sodium hydroxide, and the autoclave was sealed after adding 0.16 g of active carbon supported ruthenium (ruthenium content of 5 weight %). Thereafter, inside the autoclave was replaced with nitrogen gas, followed by hydrogen gas. After having replaced with hydrogen gas, the hydrogen pressure therein was increased to $10.8 \times 10^6$ Pa to $12.7 \times 10^6$ Pa at 45° C. to 90° C., and a reaction was allowed for 8 hours.

After the reaction was finished, the contents were taken out of the autoclave and filtered, and after removing the reducing catalyst, the composition of the reaction liquid was analyzed by gas chromatography. The analysis revealed that the reaction liquid contained 1.94 g of cyclohexylmethanol, and the conversion of benzyl alcohol was 100 mole %. Thus, the yield of cyclohexyl methanol with respect to benzyl alcohol was 92 mole %.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

What is claimed is:

1. A method of producing a benzyl ester comprising reacting a benzyl compound and a carboxylic acid by using a catalyst in which ultrafine particles including gold have been immobilized on an inorganic oxide including at least one element selected from titanium, zirconium, and aluminum in the presence of oxygen, the particle diameter of the ultrafine particles being 5 to 10 nm, the inorganic oxide having a specific surface area of not less than 50 m²/g.

2. The method as set forth in claim 1, wherein the ultrafine particles further include palladium.

3. The method as set forth in claim 1 or 2, wherein the benzyl compound has general formula (5), and the carboxylic acid has general formula $R^3COOH$, and the benzyl ester has general formula (2).

4. A method of producing a benzyl alcohol comprising hydrolyzing the benzyl ester obtained in claim 1.

5. A method of producing a benzyl alcohol of general formula (4) comprising hydrolyzing the benzyl ester obtained in claim 3.

6. A method of producing an alcohol comprising hydrolyzing the benzyl ester obtained in claim 1, and hydrogenating a hydrolyzed product.

7. A method of producing an alcohol of general formula (1) comprising hydrolyzing the benzyl ester obtained in claim 3, and hydrogenating a hydrolyzed product.

8. A method of producing an ester comprising hydrogenating the benzyl ester obtained in claim 1.

9. A method of producing an ester of general formula (3) comprising hydrogenating the benzyl ester obtained in claim 3.

10. A method of producing an alcohol comprising hydrogenating the benzyl ester obtained in claim 1, and hydrolyzing a hydrogenated product.

11. A method of producing an alcohol of general formula (1) comprising hydrogenating the benzyl ester obtained in claim 3, and hydrolyzing a hydrogenated product.

12. The method as set forth in claim 1, comprising the steps of:

adjusting pH of a solution containing a gold compound of 6 to 10;

immersing the inorganic oxide in the solution; and subjecting the inorganic oxide to a heat treatment.

13. The method as set forth in claim 12, wherein the solution containing the gold compound contains a surfactant.

* * * * *